(12) United States Patent
Willis

(10) Patent No.: US 6,314,317 B1
(45) Date of Patent: Nov. 6, 2001

(54) ELECTROACTIVE PORE

(75) Inventor: John Willis, Shirley, MA (US)

(73) Assignee: BioValve Technologies, Inc., Watertown, MA (US)

(*) Notice: Subject to any disclaimer, the term of this patent is extended or adjusted under 35 U.S.C. 154(b) by 0 days.

(21) Appl. No.: 09/507,317

(22) Filed: Feb. 18, 2000

Related U.S. Application Data (60) Provisional application No. 60/120,879, filed on Feb. 18, 1999.

(51) Int. Cl.[7] .......................................... A61N 1/30
(52) U.S. Cl. ................................. 604/20; 604/21
(58) Field of Search ........................ 604/20, 21, 500, 604/501

(56) References Cited

U.S. PATENT DOCUMENTS

| | | |
|---|---|---|
| 4,519,938 | 5/1985 | Papir . |
| 5,126,034 | 6/1992 | Carter et al. . |
| 5,147,297 | 9/1992 | Myers et al. . |
| 5,389,069 | 2/1995 | Weaver . |
| 5,484,399 | 1/1996 | DiResta et al. . |
| 5,509,410 | 4/1996 | Hill et al. . |
| 5,597,796 | 1/1997 | Brange . |
| 5,628,890 | 5/1997 | Carter et al. . |
| 5,658,444 | 8/1997 | Black et al. . |
| 5,669,874 | 9/1997 | Feiring . |
| 5,682,884 | 11/1997 | Hill et al. . |
| 5,697,901 | 12/1997 | Eriksson . |
| 5,700,481 | 12/1997 | Iga et al. . |
| 5,710,011 | 1/1998 | Forrow et al. . |
| 5,727,548 | 3/1998 | Hill et al. . |
| 5,849,174 | 12/1998 | Sanghera et al. . |
| 5,855,801 | 1/1999 | Lin et al. . |

OTHER PUBLICATIONS

Boudier, H.A.J.S., 1982, "Rate–controlled drug delivery: pharmacological, therapeutic and industrial perspectives" *Trends in Pharmacological Sciences* 3:162–164.

Kitani, A. et al., 1986, "Performance Study of Aqueous Polyaniline Batteries" *Journal of the Elecetrochemical Society* 133(6): 1069–1073.

Lane, R.F. et al., 1973, "Electrochemistry of Chemisorbed Molecules. I. Reactants Connected to Electrodes through Olefinic Substituents" *The Journal of Physical Chemistry* 77(11): 1401–1410.

Zak, J. et al., 1983, "Chemically Modified Electrodes and Electrocatalysis" *Journal of Electroanalytical Chemistry and Interfacial Electrochemistry* 150: 645–664.

Theeuwes, F, 1983, "OROS Osmsotic System Development" *Drug Development and Industrial Pharmacy* 9(7): 1331–1357.

International Search Report PCT/US00/04273, Jun. 21, 2000.

*Primary Examiner*—Sharon Kennedy
(74) *Attorney, Agent, or Firm*—Fish & Richardson P.C.

(57) ABSTRACT

Electroactive pores, devices including one or more electroactive pores are described, and methods of delivering therapeutic agents using one or more electroactive pores are described.

62 Claims, 8 Drawing Sheets

ELECTROACTIVE PORE

CROSS-REFFERENCE TO RELATED APPLICATION

This application claims priority under 35 U.S.C. §119(e)(1) to U.S. patent application Ser. No. 60/120,879, filed Feb. 18, 1999, and entitled "Drug Delivery Devices Containing An Electroactive Pore".

FIELD OF THE INVENTION

The field of the invention relates to electroactive pores, e.g., for use in the delivery of therapeutic agents.

BACKGROUND OF THE INVENTION

Certain conditions, such as hypertension, diabetes, hemophilia and other chronic conditions, can be especially taxing because they require ongoing therapeutic intervention. In many instances, patients can suffer not only the inconvenience caused by exceedingly frequent drug administration, but can also risk regular exposure to both toxic and ineffective plasma levels of drugs; toxic levels occurring soon after the drug is administered and ineffective levels occurring prior to the next scheduled administration.

Efforts have been directed toward development of controlled-release preparations such as matrixes, coated granules, or microcapsules. In addition, systems for delivery of a certain amount of drug per unit time have been developed. Systems that release drugs at a constant rate (zero-order drug delivery) are known.

One type of delivery system uses on an infusion pump for drug delivery.

SUMMARY OF THE INVENTION

In general, one aspect of the invention features a device including a member, an electroactive polymer and a biologically active transfer agent (BETA) associated with the electroactive polymer. The member has a pore passing therethrough, and the electroactive polymer is disposed so that when the electroactive polymer has a first state of charge a therapeutic agent has a first ability to pass through the pore, and when the electroactive polymer has a second state of charge different from the first state of charge the therapeutic agent has a second ability to pass through the pore different than the first ability to pass through the pore.

As used herein, the term "electroactive polymer" refers to an electrically conductive polymer. In some embodiments, an electroactive polymer is a polymer whose conductivity has been modified with one or more electron acceptor and/or electron donor dopants so that the electrical conductivity of the polymer is greater than that of the undoped polymer. In certain embodiments, an electroactive polymer is preferably substantially linear, e.g., contains few, if any, branch points or cross-links. Examples of electroactive polymers are disclosed in, for example, U.S. Pat. No. 4,519,938, which is hereby incorporated by reference.

In another aspect, the invention generally features a method of administering a therapeutic agent. The method includes passing the therapeutic agent through a device. The device includes a member, an electroactive polymer and a biologically active transfer agent (BETA) associated with the electroactive polymer. The member has a pore passing therethrough, and the electroactive polymer is disposed so that when the electroactive polymer has a first state of charge a therapeutic agent has a first ability to pass through the pore, and when the electroactive polymer has a second state of charge different from the first state of charge the therapeutic agent has a second ability to pass through the pore different than the first ability to pass through the pore. The method optionally includes charging the electroactive pore.

In a further aspect, the invention generally features a method of administering a therapeutic agent. The method includes charging an electroactive polymer. The electroactive pore is disposed relative to a pore so that when the electroactive polymer has a first state of charge the therapeutic agent has a first ability to pass through the pore, and when the electroactive pore has a second state of charge different from the first state of charge the therapeutic agent has a second ability to pass through the pore different than the first ability to pass through the pore. The method also includes passing the therapeutic agent through the pore.

In certain embodiments, the electroactive polymer is at least partially disposed within the pore, e.g, entirely disposed within the pore. In some embodiments, the electroactive polymer is at least partially disposed outside the pore, e.g., entirely disposed outside the pore.

The BETA can be associated with the electroactive pore so that electronic charge can be transferred between the BETA and the electroactive pore. The BETA can be associated with the electroactive polymer by, e.g., crosslinking, ionic bonding, covalent bonding and combinations thereof.

In general, the BETA can be an enzyme or a functional derivative of an enzyme, e.g., glucose oxidase or a functional derivative thereof.

The device can further include one or more mediators to assist in transferring electric charge, e.g., one or more mediators to assist in transferring electric charge between the member and the electroactive pore and/or one or more mediators to assist in transferring electric charge between the electroactive pore and an analyte, e.g., glucose.

The device can further include a reservoir in fluid communication with the pore. The reservoir can contain a therapeutic agent. The reservoir can be constructed from essentially any material(s) that can be molded to form a cavity. The material(s) can be flexible or inflexible.

In some embodiments, the first state of charge has a lower absolute value than the second state of charge, and the first ability of the analyte to pass through the pore is greater than the second ability of the analyte to pass through the pore.

The electroactive polymer can include aromatic molecules. The electroactive polymer can include a series of alternating single and double bonds, e.g. thiophen, phenylene diamine, pyrrole, aniline, or substituted derivatives thereof. In some embodiments, the electroactive polymer is polyaniline.

In certain embodiments, the electroactive polymer is polyaniline, and the BETA is glucose oxidase.

The membrane can be a layer of a material.

The device can further include an attachment member, e.g., an adhesive pad, a belt and/or a strap, to attach the device to a patient.

The device can also include a relatively positive element, e.g., an electrode, and a relatively negative element, e.g., an electrode, that together form a bias current within the device.

In certain embodiments, e.g., when the device is used in vivo, the device can further include a microporous needle that can extend from the surface of the skin to the interstitial fluid or to the capillary bed. Similarly, the device can include a cathether that can extend from the surface of the skin to the interstitial fluid or to the capillary bed.

The member can be electrically conductive, e.g., contain an electrically conductive material, including metals or alloys, such as gold, platinum, palladium, iridium, or combinations thereof. The member can be formed predominantly of electrically conductive material, and/or the member can be formed of an electrically non-conductive (or relatively poorly conductive) material coated with a metal or alloy, e.g., gold, platinum, palladium, or iridium, or a combination thereof.

The manner in which the electroactive polymer is charged can be varied. For example, the charge on the electroactive pore can be fixed, variable or cyclical.

Therapeutic agents that can be used in the devices and methods of the invention include, for example, vaccines, chemotherapy agents, pain relief agents, dialysis-related agents, blood thinning agents, and compounds (e.g., monoclonal compounds) that can be targeted to carry compounds that can kill cancer cells. Examples of such agents include, insulin, heparin, morphine, interferon, EPO, vaccines towards tumors, and vaccines towards infectious diseases.

The device can be used to deliver a therapeutic agent to any primate, including human and non-human primates. The device can be used to deliver an agent, e.g. a therapeutic agent to an animal, e.g., a farm animal (such as a horse, cow, sheep, goat, or pig), to a laboratory animal (such as a mouse, rat, guinea pig or other rodent), or to a domesticated animal (such as a dog or cat). The animal to which the therapeutic agent is being delivered can have any ailment (e.g., cancer or diabetes). It is expected that the device may be most useful in treating chronic conditions. However, the device can also be used to deliver a therapeutic agent (such as a vaccine) to an animal that is not suffering from an ailment (or that is suffering from an ailment unrelated to that associated with the therapeutic agent). That is, the device can be used to deliver therapeutic agents prophylactically.

The devices and methods of the invention can be used to individually tailor the dosage of a therapeutic agent to a patient.

The devices and methods of the invention can allow for outpatient treatment with increased convenience, such as, for example, without the use of an I.V.

Devices described herein can be advantageous because they can be used to promote maintenance of the concentration of a therapeutic agent in a patient's plasma within a safe and effective range. Moreover, the device can release therapeutic agents in response to the concentration of an analyte in the patient's system. Thus, the rate of drug delivery can be appropriate for the patient's physiological state as it changes, e.g., from moment to moment.

Additional advantages are provided by the design and use of the devices of the invention. For example, where a BETA are positioned within or adjacent one or more pores of a member, the BETA can be protected from external influences, such as those arising when the device is handled and used. This protection can be particularly advantageous, e.g., when the BETA is a protein, such as glucose oxidase. In such an event, it can be desirable to maintain the protein's tertiary structure in order to retain maximal biological activity. In addition, because the device can be easily replaced (e.g., a patient can apply a device to the skin every day, or every other day) the amount of a therapeutic agent (e.g., insulin) within the device can be limited. Thus, in the unlikely event the device should malfunction, the risk of serious overdose can be limited. The patient could receive, e.g., at most, only as much of the therapeutic agent as would be delivered over one or two days of administration. In the event insulin is being delivered, in some embodiments the overdose could be limited to as little as about 25 units of insulin.

Other features and advantages of the invention will be apparent from the detailed description, the figures and from the claims.

DETAILED DESCRIPTION

Figure 1:
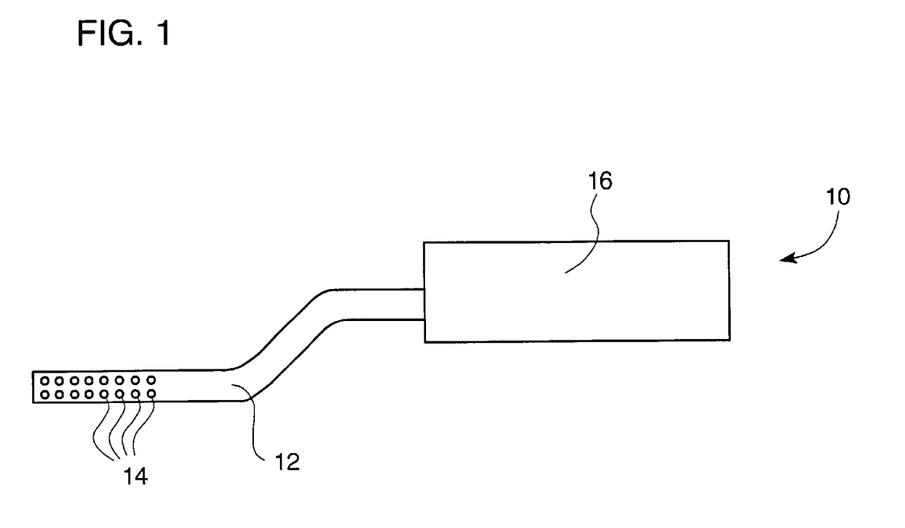
FIG. 1 is a cross-sectional view of a device according to one embodiment of the invention.

FIG. 1 is a cross-sectional view of an embodiment of a device 10 having a member 12 including pores 14. Member 12 is in fluid communication with a reservoir 16. In certain embodiments, as explained below, device 10 can be used to administer a therapeutic agent to a patient.

Figure 2:
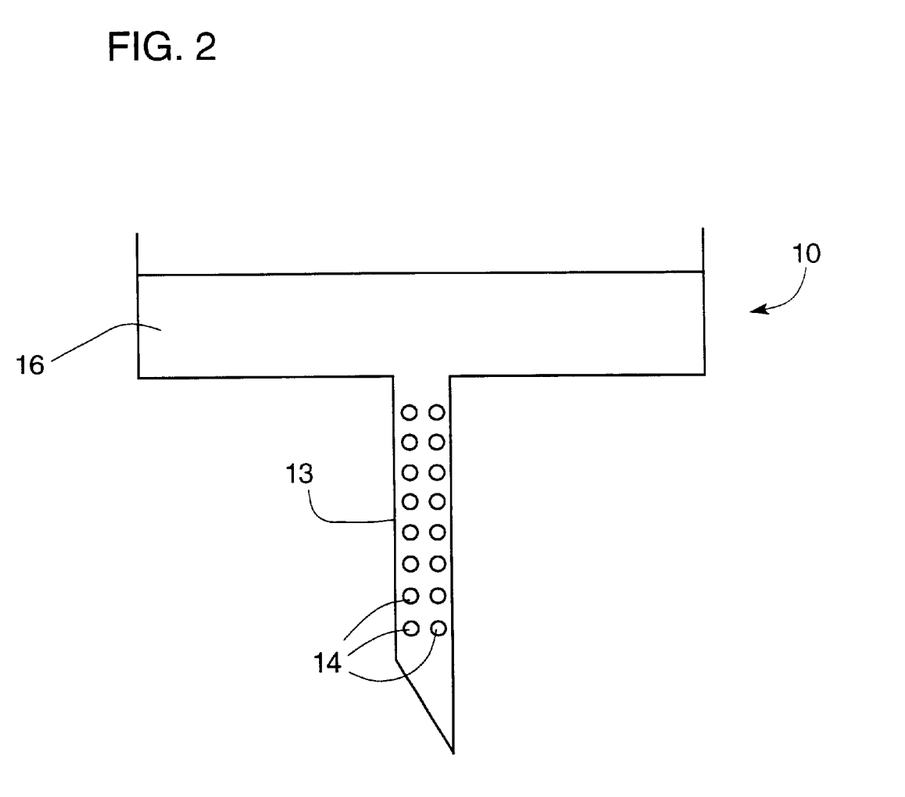
FIG. 2 is a cross-sectional view of a device according to another embodiment of the invention.

FIG. 2 is a cross-sectional view of another embodiment of device 10 having a member 13, e.g., a microporous needle, including pores 14. Device 10 also includes a reservoir 16 that is in fluid communication with member 13. In some embodiments, as explained below, device 20 can be used to administer a therapeutic agent to a patient.

Figure 3A:
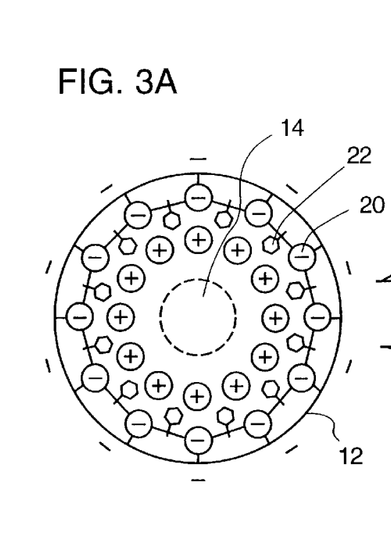
FIGS. 3A–3C are cross-sectional views of three states of relative charge of a portion of a device according to one embodiment of the invention.
Figure 3B:
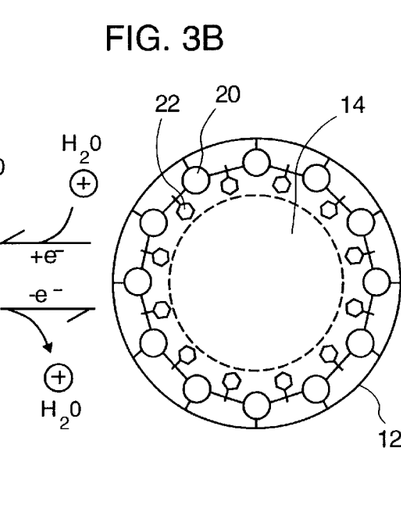
Figure 3C:
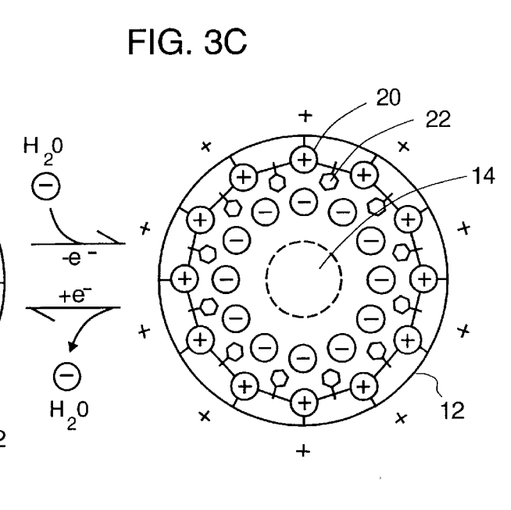

FIGS. 3A–3C show cross-sectional views of member 12 having a pore 14 with an electroactive polymer 20 and a BETA 22 when electroactive polymer 20 has different states of charge. Generally, BETA 22, electroactive polymer 20 and member 12 are arranged so that direct electron charge transfer can occur from one of these components to the next.

As shown in FIG. 3B, when electroactive polymer 20 has a relatively small state of charge, e.g., the absolute value of the charge on electroactive polymer 20 is relatively small, the cross-sectional region in a direction parallel to a portion of pore 14 that is blocked by electroactive polymer 20 is relatively small.

As shown in FIGS. 3A and 3C, however, when electroactive polymer 20 has a relatively large state of charge, e.g., the absolute value of the charge on electroactive polymer 20 is relatively large, the cross-sectional region in a direction parallel to a portion of pore 14 that is blocked by electroactive polymer 20 is relatively large.

Device 10 can be used to administer a therapeutic agent present in reservoir 16 to a patient by disposing pores 14 in the patient's subcutaneous tissue. Device 10 can be advantageously used because delivery can be controlled by the state of charge of electroactive polymer 20 which, in turn, can be controlled by the concentration of an analyte present in the patient's blood. In some embodiments, the analyte of interest is a species, e.g., a molecule or an ion, present in the patient's blood that associates with BETA 22. As described below, the association between the analyte and BETA 22 can include electron transfer between BETA 22 and the analyte. Such electron transfer can change the state of charge of electroactive polymer 20, thereby altering the ability of the therapeutic agent to pass through pores 14. For example, where one wishes to detect glucose, BETA 22 can be glucose oxidase, or a functional derivative thereof.

A. The Member

Generally, the member can be formed of any material that can serve as a partition between a therapeutic agent and a patient's system, the pores being of sufficient size and density to allow the therapeutic agent to move from one side of the partition (i.e., the side facing the therapeutic agent) to the other (i.e., the side facing the patient's system). As described further below, this movement can be controlled in part by an electroactive polymer coating that is applied to the member in embodiments where such a coating is used.

The member can be an electrical conductor, a semiconductor, or an electrical non-conductor. Conductive members include, but are not limited to, carbon cloth or felt, expanded metal or metal mesh sheets, or differently configured metallic shapes (e.g., cylinders or cones consisting of metal mesh or metal sheets containing microholes). The metal can be, e.g., a noble metal, such as gold, platinum, or palladium. The metal can also be a base metal, such as steel, nickel, or titanium. The base metal can be coated with a noble metal, e.g., with gold, platinum, or palladium, or a combination thereof. Conductive alloys can also be used.

Materials useful as non-conductive members include, but are not limited to, silicon, glass, plastic, ceramic, mylar, or membranes, such as those commercially available from companies that supply materials to molecular biologists. Such membranes can be sold under tradenames, e.g., NUCLEOPORE7 (a polycarbonate or polyester membrane containing uniform cylindrical pores), CYCLOPORE7, ANOPORE7, and MILLIPORE7. When one chooses to create reasonably uniform pores (rather than purchase and use a material such as the membranes described above), laser machining can be performed to create pores having a reasonably uniform diameter and density.

Generally, the member should be thick enough to be practically incorporated within a device (i.e., it should be thick enough to withstand application of an electroactive polymer coating without tearing or being otherwise damaged). In certain embodiments, the thickness of the membrane (or of any other material used as a member) can range, e.g., from about one micrometer to about 20 micrometers (e.g., about 10 micrometers).

The diameter of the pore can be chosen such that, when coated with an electroactive polymer in an uncharged state, it can be open. The diameter of the pores within the membrane (or within any other material used as a member) can vary, e.g., from about 0.1 micrometer to about 10 micrometers (e.g., from about 1.0 micrometer to about 8.0 micrometers, such as from about 4.0 micrometer to about 6.0 micrometers).

The pore density (i.e., the number of pores per unit area) can vary and, in certain embodiments, the pore density can be partly dependent on the pore diameter. Generally, the size of the pores and their density is inversely proportional (the larger the pores, the lower the required density). In some embodiments, pore size and density can be regulated such that an appropriate amount of a therapeutic agent can move across the member in response to an analyte (as described further below). In certain embodiments, the pore density can range from about $1 \times 10^5$ pores per square centimeter to about $3 \times 10^8$ pores per square centimeter.

Non-conductive members can be coated (e.g., by plating, sputtering, vapor deposition, or the like) with metal, carbon, graphite, or a like material (See Example 1, below). Similarly, a non-conductive member can be covered with metallic paste. The non-conductive surface can either be entirely or partially coated with conductive material. For example, the conductive material can be patterned around the pores of a non-conductive member by methods known in the art (e.g., by screen printing, ink jetting, or photolithography).

In some embodiments, the thickness of the material applied to the non-conductive surface can be taken into consideration when determining whether the diameter of the pore is sufficient to allow passage of a therapeutic agent contained within the device. In certain embodiments, the thickness of the material can be from about 100 nanometers to about 500 nanometers.

In some embodiments, the non-conductive surface can be coated on one side with an electrically conductive material either before or after the other side has been coated with an electroactive polymer.

An electrode can be prepared by using an electrically conductive member or by immobilizing electrically conductive molecules on the surface of a non-conductive member. Methods of preparing such electrodes are disclosed, for example, in Zah and Kuwana, (*J. Electroanal. Chem.* 150:645, 1983), Miller, ed. (*Chemically Modified Surface in Catalysis and Electroanalysis,* ACS Symp. Ser. 192, American Chemical Society, Washington, D.C., 1982), Fujihara (*in Topics in Organic Electrochemistry,* A. J. Fry and E. Britton, eds., Plenum Press, NY, 1986, at page 255), Lane and Hubberd (*J. Phys. Chem.* 77:1401, 1978), Merz and Kuwana (*J. Electroanal. Chem.* 100:3222, 1978), which are hereby incorporated by reference.

The member itself can be an electroactive polymer formed by solution coating methods, such as described, for example, in U.S. Pat. No. 4,519,938, which is hereby incorporated by reference.

The member can be incorporated into a probe, e.g., a probe that can be inserted into the body, e.g., into the subcutaneous tissue. The member that supports the electroactive pore can be fashioned along the sides of a needle (e.g., a microneedle) or a catheter, e.g., a needle or catheter such as those used in the context of drug delivery, such as disclosed, for example, in U.S. Pat. No. 5,697,901, which is hereby incorporated by reference.

In certain embodiments, the microneedle can have a diameter of about 300 micrometers.

In some embodiments, a microneedle suitable for use in the device can have a beveled tip and one or more microneedles can be mounted on the portion of the device that contains a therapeutic agent. In certain embodiments, the beveled tip can taper to a zero diameter along the two millimeters closest to the tip.

Microneedles including an interface region and a shaft having a microflow channel therein can be used and are described in, for example, U.S. Pat. No. 5,855,801, which is hereby incorporated herein by reference.

B. The Electroactive Polymer

Devices described herein can include an electrically conductive polymer. These polymers can function as molecular wires that promote electron transfer between the BETA (described below) and another element, e.g., the member (described above). The electroactive polymer can promote electron transfer between the redox center of the BETA and the member. This transfer can occur in either direction (from the BETA, through the electroactive polymer to the member; or from the member, through the electroactive polymer, to the BETA). In the latter case, the redox state of the BETA can be modulated by an electrode potential carried through the electroactive polymer. In the event the BETA is an enzyme, the enzyme's biological activity can depend on the electrode potential. This mechanism can regulate the activity of the BETA through electric stimulation (e.g. the application of a bias potential to the device is described below).

In the unmodified state, the backbone of an electroactive polymer can possess oxidizable and/or reducible moieties. When a voltage is applied to the electroactive polymer, the backbone can undergo reduction (n-type), thereby attaining a net negative charge. The backbone can also undergo oxidation (p-type) thereby attaining a net positive charge. Some electroactive polymers may contain both reducible and oxidizable moieties within their backbone. Depending on the voltage applied, these electroactive polymers can undergo either reduction or oxidation.

In some embodiments, to maintain electrical neutrality, counter ions and associated water molecules within the surrounding electrolyte solution can move (as in electrophoresis or electroosmosis) into the electroactive polymer network. This can cause the electroactive polymer network to swell, which can reduce the ability of a material, e.g., a therapeutic agent, to pass through the pores. This process can be at least partially reversible. If the voltage is reversed and the state of charge on the electroactive polymer is brought back toward the state of charge on the electroactive polymer in its prior state, water and counter ions can move out of the electroactive polymer and back into the electrolyte solution. This can cause the electroactive polymer network to shrink, which can increase the ability of a material, e.g., a therapeutic agent, to pass through the pores. This process is described, for example, in Salehpoor et al., SPIE 3040:192–198, 1997, and publications cited therein, which are incorporated herein by reference.

In some embodiments, at a constant applied voltage, the electroactive polymer can remain in an electrically balanced state, e.g., swollen, until the voltage is reversed and the electroactive polymer relaxes or shrinks as its state of charge is reduced.

In certain embodiments, for a molecule that exhibits reversible or partially reversible redox behavior, e.g., certain BETA, that is associated with the charged electroactive polymer backbone, electron transfer between the BETA and the electroactive polymer backbone can occur. A BETA is associated with an electroactive polymer when it is so disposed that electric charge can be transferred between the BETA and the electroactive polymer. Association of the BETA to the electroactive polymer can involve, e.g., entrapping the BETA within the electroactive polymer, adsorbing the BETA on the electroactive polymer, ionically bonding the BETA on the electroactive polymer, physically bonding the BETA on the electroactive polymer, and/or covalently linking the BETA to the electroactive polymer.

In some embodiments, association of the BETA with the electroactive polymer brings the BETA to within, e.g., about 5 angstroms, about 10 angstroms, about 20 angstroms, about 40 angstroms, or about 50 angstroms, of the electroactive polymer.

Where an analyte that specifically oxidizes or reduces the BETA is present in the solution of interest, e.g., the patient's blood, electron transfer can occur from the analyte to the BETA, to the electroactive polymer and, ultimately, to the member.

Although not wishing to be bound by theory, it is believed that in some embodiments if the rate of electron transfer from the BETA to the electroactive polymer is greater than the rate of electron transfer from the member to the electroactive polymer (or vice versa), some or all of the charge which thereby accumulates on the electroactive polymer will be neutralized by the influx of counter ions. As a result, the electroactive polymer will become less swollen and the ability of a material, e.g., a therapeutic agent, to pass through the pores will increase. As the concentration of analyte generally decreases, the amount of charge transferred to the electroactive polymer decreases, decreasing the ability of a material, e.g., a therapeutic agent, to pass through the pores. As the concentration of the analyte increases, the amount of charge transferred to the electroactive polymer increases, increasing the ability of the material to pass through the pores. This combination of oxidation/reduction can cause modulation of the ability of the material to pass through the pores.

Electroactive polymers can be formed from monomers. For example, electroactive polymers can be formed from cyclic aromatic compounds such as pyrrole, substituted pyrrole derivatives, thiophene, substituted thiophene derivatives, furan, indole, isoquinoline, azulene, aniline, and substituted aniline derivatives, or combinations thereof. Polyaniline can be used as an electroactive polymer in battery electrodes, such as disclosed in, for example, Kitani et al., J. Electrochem. Soc. 133:1069–1073, 1986, which is hereby incorporated by reference.

In certain embodiments, the electroactive polymer can be coated as follows. A buffer solution containing one molar Bes, pH 7.0 or 7.4 phosphate buffered saline is formed. Pyrrole is added to the buffer and stirred until it dissolved. The concentration of pyrrole is from about five volume percent to about six volume percent. Glucose oxidase (about one volume percent to about three volume percent) is added and stirred until it dissolved. Other proteins can optionally be added (e.g., BSA and/or Byco C). The buffer, enzyme and pyrrole solution is then placed in a cell with a reference electrode (e.g., a silver/silver chloride reference electrode), a counter electrode (e.g., a platinum electrode), and a working electrode (e.g., a platinum electrode). The solution in the cell is not stirred. A potential of from about 0.4V to about 0.6V relative to the silver/silver chloride reference is applied to the platinum electrode until from about 200 microcoulombs to about 3000 microcoulombs passed, at which point the applied voltage is turned off. The working electrode is then removed, rinsed in phosphate buffer and dried in a 60° C. oven for from about 15 minutes to about 30 minutes. Typically, a membrane solution containing polyurethane dissolved in tetrahydrofuran is dip coated onto the wire. The electrode with the polyurethane coat is dried at room temperature for about 15 minutes, then at 60° C. oven for about 15 minutes. The electrode is then tested in a buffer solution to which incremental levels of glucose is added to obtain a dose response curve.

In some embodiments, the electroactive polymer can be stable in both air and water.

In embodiments, pyrrole is used as the monomer for producing an electrically conducting polypyrrole coating.

Examples of certain monomers and polymers that can be used are shown in FIGS. 4A–4F.

Figure 4A:
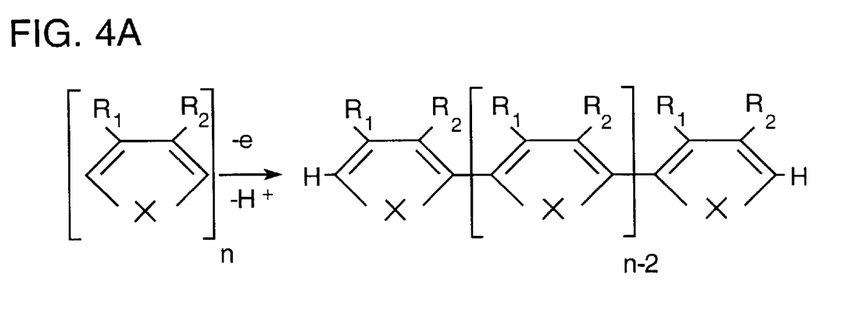
FIGS. 4A–4F are illustrations of monomers and polymers useful in a device according to the invention.

In FIG. 4A, where X is SH, the monomer is thiophene; where X is O, the monomer is furan; when X is NH and $R_1$ and $R_2$ are H, polypyrrole is formed.

Figure 4B:
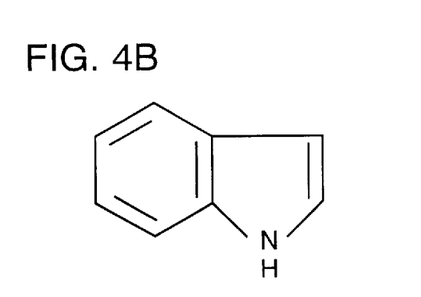

An indole monomer is shown in FIG. 4B.

Figure 4C:
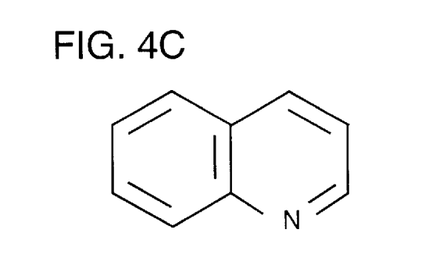

An isoquinoline monomer is shown in FIG. 4C.

Figure 4D:
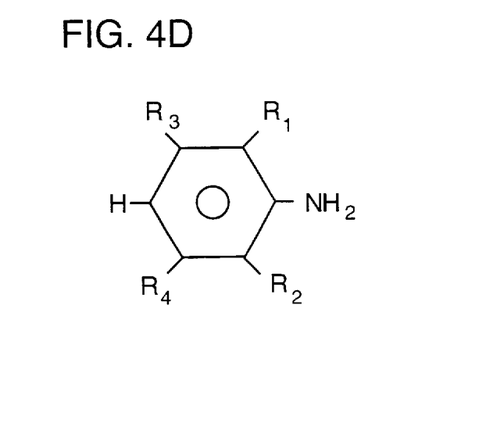

The aromatic compound shown in FIG. 4D is aniline (when R1, R2, R3, and R4 are H), which can be assembled to form linear or branched polymers.

Figure 4E:
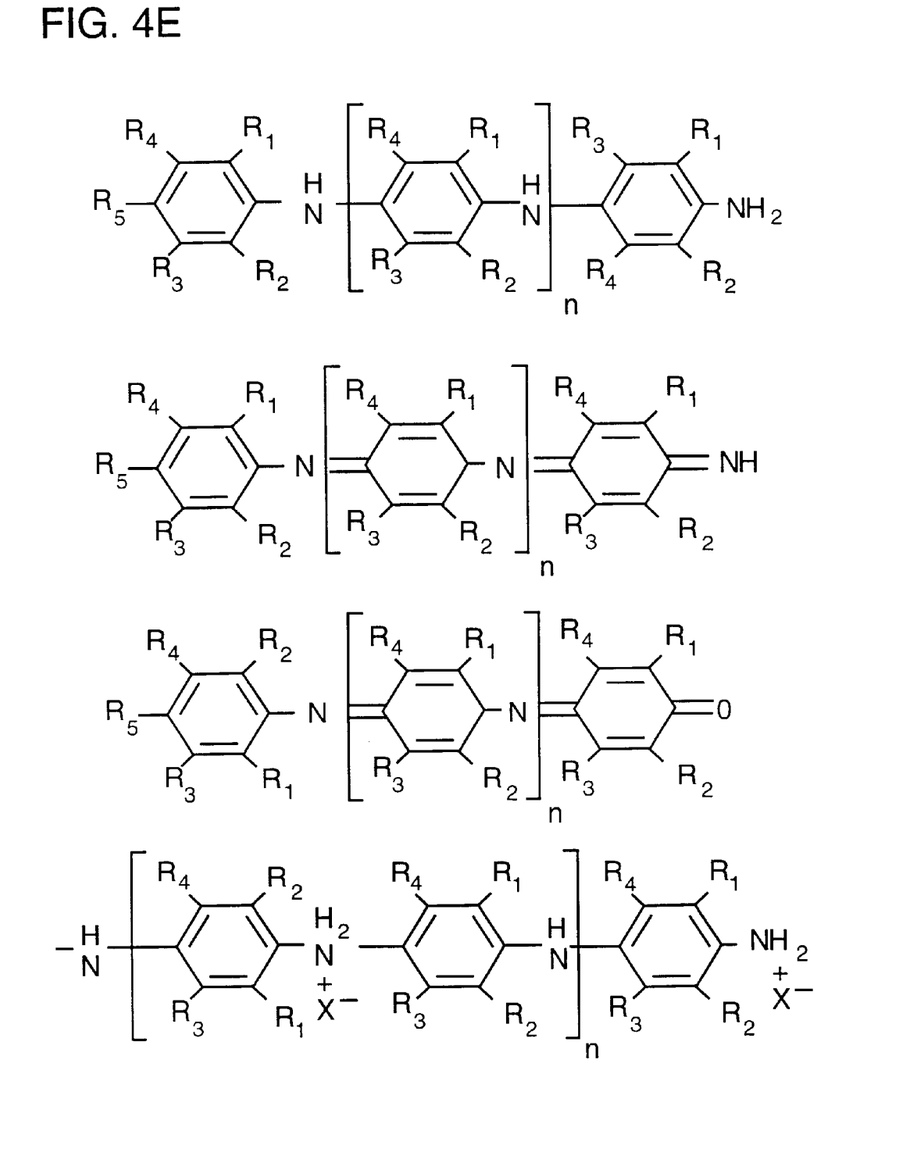

Four examples of linear polyanilines (where $R_1$ to $R_5$ are H) are shown in FIG. 4E.

Figure 4F:
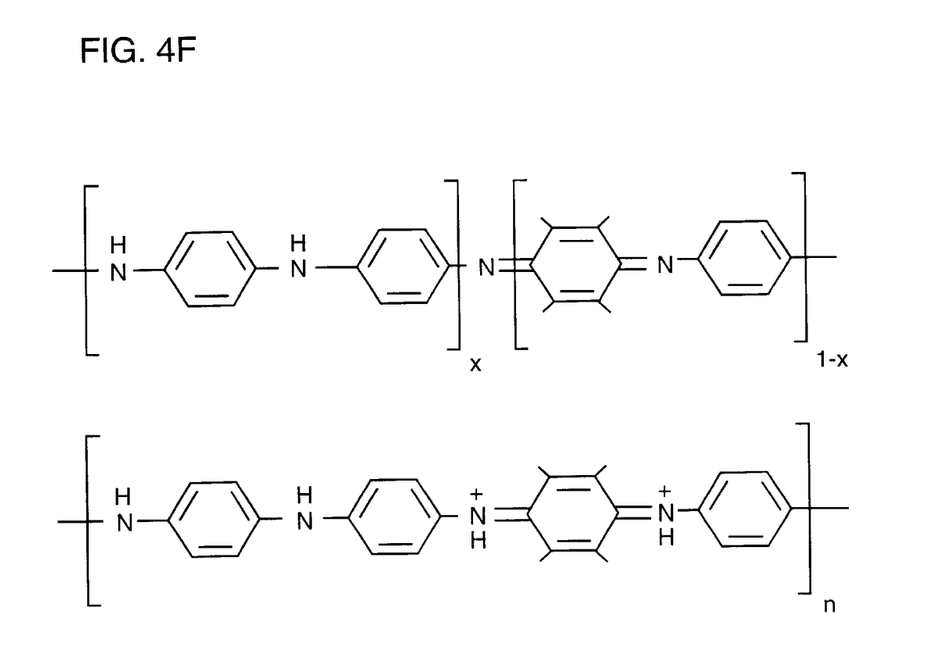

FIG. 4F shows two examples of mixed state polymers.

In addition to the R groups present in the monomers described above, substituted polymer derivatives can be formed by using, for example, one or more of the following R groups: —OCH$_3$, —OR, —CH$_3$, —C$_2$H$_5$, —F, —Cl, —Br, —I, —NH$_2$, —NR, —NHCOR, —OH, —O—, —SR, —OCOR, —NO$_2$, —COOH, —COOR, —COR, —CHO, —CN, —(CH$_2$)$_n$—CH$_3$ (e.g., where n is from 0 to 12).

The electroactive polymer can be applied to the member by physical association. The association can be one which allows the electroactive polymer to adhere to the member. For example, the member can be dipped in a solution containing the electroactive polymer. Similarly, an electroactive polymer-containing solution can be sprayed onto the member.

Alternatively, the electroactive polymer can be deposited by polymerization of monomers dissolved in solution, e.g, by oxidizing chemical polymerization. For example, one can place a pyrrole solution in water (e.g., from about 0.3 molar to about 0.8 molar pyrrole) on one side of the member (e.g., a membrane) and an iron(III) chloride solution in water (e.g., from about 1.5 molar to about 2.5 molar) on the other. The pyrrole can be polymerized by contacting the two solutions with the member (e.g., the pores of the member).

As known to those skilled in the art, the time for polymerization can vary depending upon the particular materials used. For example, a time period of from about two minutes to about 10 minutes can be used. In certain embodiments, time periods appreciably longer than 10 minutes can result in formation of essentially nonporous members, which can limit its usefulness in the device of the invention.

The polymerization reaction can be stopped, for example, by rinsing with water or a phosphate buffered saline, e.g., PBS, pH 6.5.

In some embodiments, an electrochemical reaction can bring about polymerization on the member. For example, the first step in electrochemical polymerization of pyrrole can be generation of a radical cation at the anode. Chain propagation can then proceed by reaction of two radical cations, pairing the spins and elimination of two protons to produce the neutral dimer. At the potentials used to oxidize the monomer, it can be possible to oxidize the dimer and higher oligomers to the corresponding radical cation. Chain propagation can continue by reaction of the oligomer radical cation primarily with the radical cation of the monomer, which can be present in high concentration in the region of the anode. As the chain grows, the pyrrole oligomer can become insoluble and precipitate out on the electrode, e.g., the member, where the chain can continue to grow until the oligomer radical cation becomes too unreactive or until it becomes prevented from reacting by stearic hindrance.

The polypyrrole coat formed by electrochemical synthesis from a solution of pyrrole and sulfuric acid in water can be in the oxidation state of one positive charge for three to four pyrrole rings. Its conductivity can be about 8 S/cm. The coat made in a nonaqueous medium containing pyrrole and N(Et)$_4$BF$_4$ in CH$_3$CN can be in the oxidation state of one positive charge for four to five pyrrole rings, with a conductivity of about 100 S/cm.

Other materials can be used in a similar fashion, such as thiophene, furan, indole, and azulene, which can also undergo electrochemical polymerization and oxidation to yield oxidized polymers of varying conductivities.

Aniline can also be electrochemically polymerized in an acidic aqueous solution to yield a conductive polyaniline membrane on the surface of a member. For example, electrochemical polymerization can be performed in a glass electrochemical vessel equipped with three electrodes ( a working electrode, a counter electrode, and a reference electrode). The potential of the working electrode can be controlled at +1.2 versus a reference electrode (e.g., a Ag/AgCl reference electrode) with a potentiostat, and an aqueous solution containing aniline and a BETA (e.g., an enzyme) can be added to the vessel. Electrolysis can continue until a fixed charge is passed. The total charge passed can control the thickness of the electroactive polymer coating on the member. This procedure demonstrates that in certain embodiments, the electrochemical polymerization and deposition of monomers can be carried out in the presence of a BETA.

Figure 5:
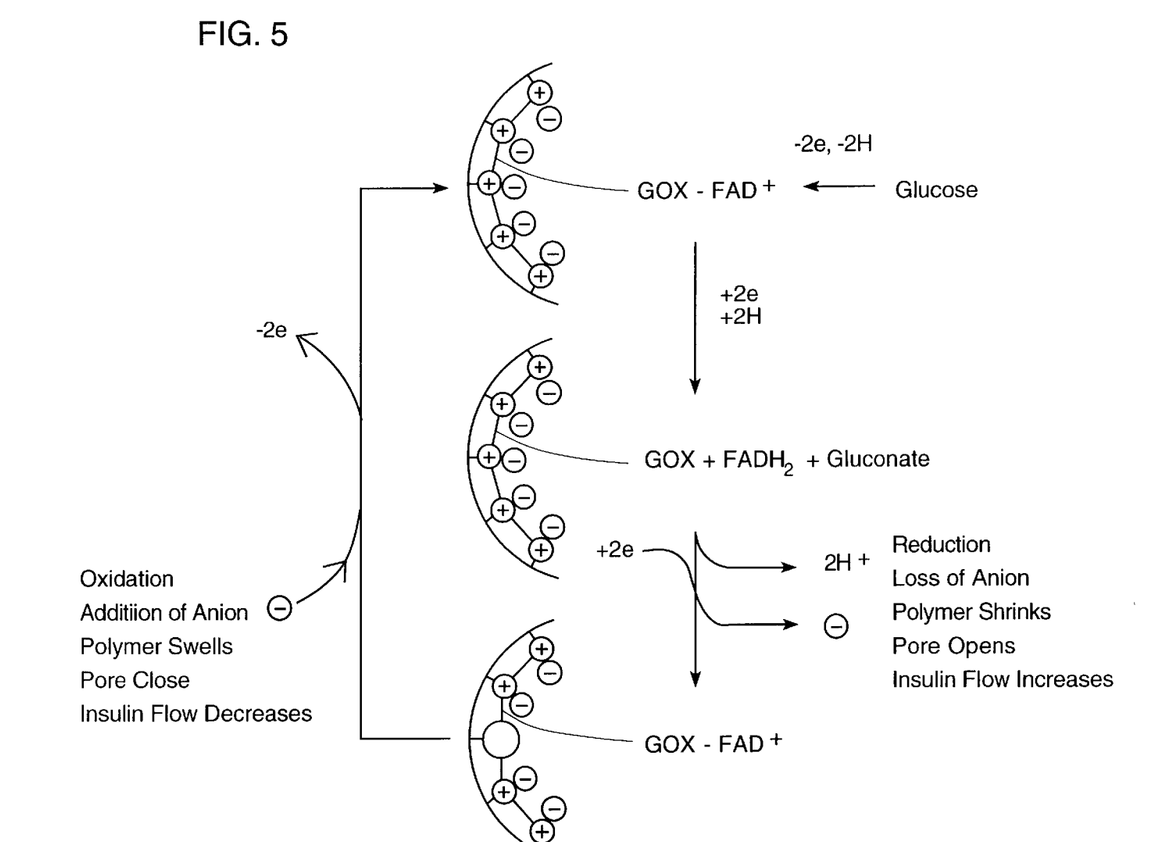
FIG. 5 is a schematic representation of the interaction of glucose with a device according to one embodiment of the invention.

The BETA glucose oxidase has been successfully entrapped in polyaniline polymerized on the surface of a platinum member and shown to retain its biological activity. Moreover, the membrane formed is permeable to small molecules such as oxygen and H$_2$O$_2$ but not to larger molecules. Accordingly, when a device contains a member, polyaniline (electroactive polymer), and glucose oxidase (BETA), glucose levels can be monitored by monitoring the change in the oxygen-reducing current or hydrogen peroxide oxidizing current that is produced upon consumption of oxygen, which occurs subsequent to the interaction between glucose and glucose oxidase. (See FIG. 5).

When a polymerization reaction is complete, the extent of polymerization can be assessed, if desired, by examining the coated member with a scanning electron microscope. The thickness of the electroactive polymer layer within the pores can depend, for example, on the diameter of the pores. In some embodiments, a device having pores that are substantially closed will prevent at least 80% (e.g., 85%, 90%, 95%, or even 99%) of the therapeutic agent contained therein from exiting the device under physiological conditions of use (i.e., when applied to a patient) within a 24 hour period of time.

The redox potential of a polymer is normally lower than that of the corresponding monomer(s) from which it was formed. Thus, in some embodiments, synthesized polymers can be electroconductive without further doping.

C. The Beta

A biological molecule that is capable of acting as a BETA can be associated with the electroactive polymer. Suitable BETA generally include enzymes, and functional derivatives thereof. BETA can be incorporated into the devices described herein by methods similar to those used to incorporate monomers (thereby forming a conductive polymer network).

BETA can be selected, for example, from among those that participate in one of several organized electron transport systems in vivo. Examples of such systems include respiratory phosphorylation that occurs in mitochondria and the primary photosynthetic process of thyrakoid membranes.

BETA can specifically interact with a metabolite or analyte in the patient's system. For example, BETA-analyte pairs can include antibody-antigen and enzyme-member.

Redox enzymes, such as oxidases and dehydrogenases, can be particularly useful in the device. Examples of such enzymes are glucose oxidase (EC 1.1.3.4), lactose oxidase, galactose oxidase, enoate reductase, hydrogenase, choline dehydrogenase, alcohol dehydrogenase (EC 1.1.1.1), and glucose dehydrogenase.

The BETA can be associated with the electroactive polymer by techniques known in the art. The association can be such that electrons can flow between the BETA and the electroactive polymer. In addition to the methods described above, the BETA and the electroactive polymer can be associated, e.g., by entrapment, crosslinking, ionic bonding, or covalent bonding. The member to which an electroactive polymer has been affixed can be treated with a redox enzyme-containing solution by, e.g., exposing the member-polymer to the solution, with agitation, at 2EC to 10EC for at least 5 minutes and preferably up to 30 minutes. The concentration of the redox enzyme in solution can vary and, in certain embodiments, is preferably about 5 mg/ml. Following this treatment, the prepared device can be dried overnight in a desiccator over $CaCl_2$.

Where glucose oxidase is the BETA, it can be present at from about 0.02 U per square centimeter to about 0.2 U per square centimeter of surface (where 1 unit is the amount of enzyme required to oxidize 1 imol of â-D-glucose per minute at pH 5.1 and at a temperature of 35EC).

Devices described herein can exhibit specificity for a given analyte; and the specificity can be imparted by the selective interaction of an analyte (e.g. glucose) with the BETA (e.g., glucose oxidase or glucose dehydrogenase).

D. The Bias Potential

A bias current or voltage, e.g., a fixed, variable, or cyclical current or voltage, can be applied to the device (e.g., to the surface of the member). The bias potential can be determined empirically. Typically, the magnitude of the applied voltage ranges from +/−1.0 volt vs. Ag/AgCl. The magnitude of the current can range from 1.0 picoamp ($10^{-12}$ amps) to 1.0 amp (e.g., the current can range from 100 picoamps to 0.1 amp). When such a field is established, the device can emulate a working electrode (or indicator electrode) in an electrochemical cell consisting of a cathode and an anode, with or without a reference electrode. A counter electrode can, e.g., be constructed from carbon, graphite, platinum, silver, like metals, or mixtures thereof. A reference electrode can, e.g., be constructed from silver or silver chloride.

At a given current or voltage, the change in the redox state of the electroactive polymer will be proportional to the amount of analyte that interacts with the BETA (the amount of the analyte that interacts with the BETA is, in turn, proportional to the concentration of an analyte, e.g., an analyte in a patient; e.g., the higher the concentration of glucose in a patient's bloodstream, the more glucose will interact with glucose oxidase in the device).

In one embodiment, one can detect (and thereby monitor) the concentration of an analyte in a patient by examining the state of the device (ie., the change in the bias potential).

The bias potential may be set to maintain a constant release of therapeutic agent from the reservoir within the device (such as would maintain a basal level of an analyte). Constant release can be achieved by determining the electrochemical properties of the BETA-electroactive polymer combination. For example, by performing solution experiments using cyclic voltammetry, redox potentials can be obtained. The current maximum in a cyclovoltammetric peak indicates the potential at which the reduction or oxidation reaction is proceeding at its maximum diffusion limited rate. When the potential across the device is set at this value, the on/off actuation of the device may be so rapid that little drug is dispensed. However, if the bias potential is set below the diffusion limited value, charge accumulation within the device can occur. Under conditions where charge accumulation occurs, the opening within the pores is increased, allowing for greater release of the therapeutic agent contained within the device into a patient's system. As the accumulated charge decreases, the opening within the pores is decreased, until the level of the basal current is reached.

The bias potential can be controlled by a computer, e.g., a microprocessor within the device or elsewhere (e.g., at a remote location).

E. The Reservoir and Ejection of Therapeutic Agents

A device described herein can also have a reservoir for containing a therapeutic agent. The reservoir may take the form of a chamber that can be expanded or contracted; expanded when filled with a therapeutic agent and contracted to dispense or expel the agent. Typically, the reservoir will accommodate 0.2–10.0 ml of a solution or suspension containing a therapeutic agent (e.g., the reservoir can contain 0.4, 0.5, 1.0, 2.5, 5.0 or 7.5 ml of such a solution). The reservoir and therapeutic agent can be chosen such that the device contains not more than 1, 2, 3, 5, or 10 days supply of the agent.

The reservoir can also be divided so that an agent, e.g., a therapeutic agent, can be stored in one compartment and a solution, e.g., an aqueous solution such as a saline solution can be stored in a second compartment. The division between the cavities or compartments in the reservoir would then be broken prior to use so that the therapeutic agent comes into contact with the solution.

Optionally, the device can include a pump or similar device for positively ejecting a therapeutic agent from the reservoir in which it is stored. The pump can be, e.g. a mechanical or partially mechanical device, as described below, that exerts pressure on the reservoir so that the therapeutic agent therein is ejected through the pores of the device, into the patient's system. The pressure exerted by the pump can be regulated by the current generated when an analyte specifically interacts with a BETA. For example, in a device designed for treatment of diabetes mellitus, the higher the patient's blood glucose level, the more glucose will interact with glucose oxidase or glucose dehydrogenase within the device, and the greater the current generated by the transfer of electrons from glucose, to glucose oxidase, to the electroactive polymer within the membrane, to the electrically conductive member beneath. The greater this current, the greater the signal conveyed to the pump, and the more insulin will be ejected from the reservoir into the patient's system. As the patient's blood glucose levels fall in response to the newly presented insulin, the current generated across the device will fall, and the pump will, accordingly, drive less insulin into the patient's system.

The source of the pressure exerted by the pump can be an electrical actuator, such as a piston whose speed and/or stroke is modulated, as described above, by the concentration of an analyte in the patient's system. Alternatively, the piston can be driven by an analyte-modulated chemical or physiochemical reaction (e.g., electrolysis of $H_2O$) that produces a gas that drives the piston.

Osmotic Pumps

Elementary osmotic pumps are known in the art (see, e.g., Theeuwes, *Drug Dev. & Indust. Pharm.* 9:1331–1357, 1983; Boudier, *Trends in Pharmacol. Sci.* pp. 162–164, April 1982, which are hereby incorporated by reference). These pumps were developed in response to the need to maintain the concentrations of drugs in a patient's plasma, particularly those that require chronic administration, within a safe and effective range. Conventionally, patients receive their medication by bolus administration (e.g., by injecting or otherwise administering a set amount of a drug). Immediately after such administration, the plasma level of the drug can exceed the maximum level for safety. But before the next scheduled administration, the level can fall below the minimum level required for effectiveness. As a result, patients are repeatedly exposed to both toxic and ineffective concentrations of drugs. The ratio of these two levels (the maximum level for safety and the minimum level for effectiveness) is known as the therapeutic index. While these fluctuations can be minimized by dosing at frequent time intervals, the required regimen can be extremely inconvenient for the patient (particularly where the drug has a short half-life).

Examples of delivery systems in which osmotic pressure is the driving force behind drug release include PROGESTASERT7, a contraceptive system that releases progesterone to the uterine lumen at a rate of 65 microgram per day for one year, and OCUSERT7, an ocular system that releases pilocarpine to the eye at rates of 20 or 40 micrograms/hour for one week. Similarly, an elementary osmotic pump, such as described by Theeuwes (supra) can be used to dispense therapeutic agents into the gastrointestinal (GI tract at a rate independent of external factors such as GI tract pH and motility. These systems illustrate two of the most prominent advantages of osmotic minipumps: constant and prolonged delivery of a drug at a predetermined rate and the ability to target delivery to a particular tissue or organ.

Structurally, osmotic pumps can include a solid core, semipermeable membrane and an orifice for drug delivery. Osmosis is the force driving expulsion of a drug from the device: water imbibed, e.g., from the environment, crosses the membrane at a controlled rate and causes the drug solution to exit through the delivery orifice. Delivery rate is controlled by osmotic properties of the core and membrane area, its thickness, and permeability to water.

In another embodiment, the change in the charge of the electroactive polymer within the pores of the device can serve as a self-regulating osmotic pump. Charge neutralization can occur by migration of water and ions into and out of an electroactive polymer (i.e., by doping and undoping), thereby creating an osmotic pumping action.

Expulsion of a Therapeutic Agent from the Device

When one or more therapeutic agents are contained within the device and have access to the pores of the device (the agent(s) will be positioned so that they can move through the pores and into a patient's body), modulation of the diameter of the pore can, alone, be sufficient to allow sufficient movement of the agent(s) into the outer electrolyte solution.

In another embodiment, the modulated current generated by charging the electroactive polymer in response to the level of analyte can be used to control an electromechanical pump that, when activated, forces the agent(s) through the open pore and into the outer electrolyte solution. Thus, in effect, the analyte level modulates both the pore opening and the pumping force. This double feedback redundancy is an added safety feature of the system. If, for some reason, the pump failed to shut off at the appropriate time, the declining analyte concentration would cause the pore to close. When pressure within the reservoir containing the therapeutic agent(s) increases to a pre-set level, electrical contact to the pump is shut off until the pressure falls back to within its normal range of operation. If the pore fails to close as the analyte level falls (in response to infusion of the therapeutic agent(s)) the current generated by charging the electroactive polymer will also fall and the pump will gradually shut down.

If electron transfer between the BETA and the electroactive polymer is slower than between the member and the electroactive polymer, and if the applied potential across the polymer network is pulsed, then pulsing of the pore opening can also be achieved. During the "off" period, all or part of the polymer can be reduced or oxidized by the BETA so that the polymer returns to its virgin state. This opens the pore. The amount of charge transferred between pulses determines the size of the pore opening. When the potential is again turned on, the polymer is again fully charged and it closes.

In effect, this on/off cycling can cause a pumping action. Thus, the pore size and the pumping action are modulated by the amount of analyte in the outer electrolyte solution. If a therapeutic agent was dissolved and stored on the inner side of the pore, pulsing of the pore could force the agent from inside the pore to the outer electrolyte solution. If the level of analyte was modulated by the amount of drug in the outer solution, the combination of the processes above would constitute a self-regulating drug delivery device. As in the case described above, pumping of the drug could be done through use of a conventional electromechanical pump.

In another embodiment, self-regulated pumping can be achieved by storing therapeutic agent(s) within a collapsible reservoir. As the pore open, the natural tendency would be for the drug to move from a solution of high concentration to a solution of low concentration until equilibrium is achieved. Modulation of the pore opening may also be used to regulate the amount of water imbibed by a collapsible reservoir surrounding the drug reservoir. Water imbibed when the pore is open causes the volume within the osmotic reservoir to increase, thereby forcing the therapeutic agent (s) out of the device.

Attachment of a Device

The device itself can be used in a number of environments. It can be used in vivo or ex vivo (e.g., in a cell culture environment). In the event the device is used in vivo it may be wholly or partially internalized in a patient's body. For example, the device can include an adhesive component and a probe that extends beneath the body surface. When a portion of the device is worn externally, it can be attached to the patient by a belt, strap, or adhesive (e.g., it can be attached to the patient's skin by an adhesive patch). In some instances, an adhesive and a second security device (e.g., a belt or strap) can be used.

The amount of therapeutic agent carried within the device can vary. The amount can include less than 1, less than 2, less than 5 or less than 10 days supply of a therapeutic agent or agents.

Test Apparatus

Figure 6:
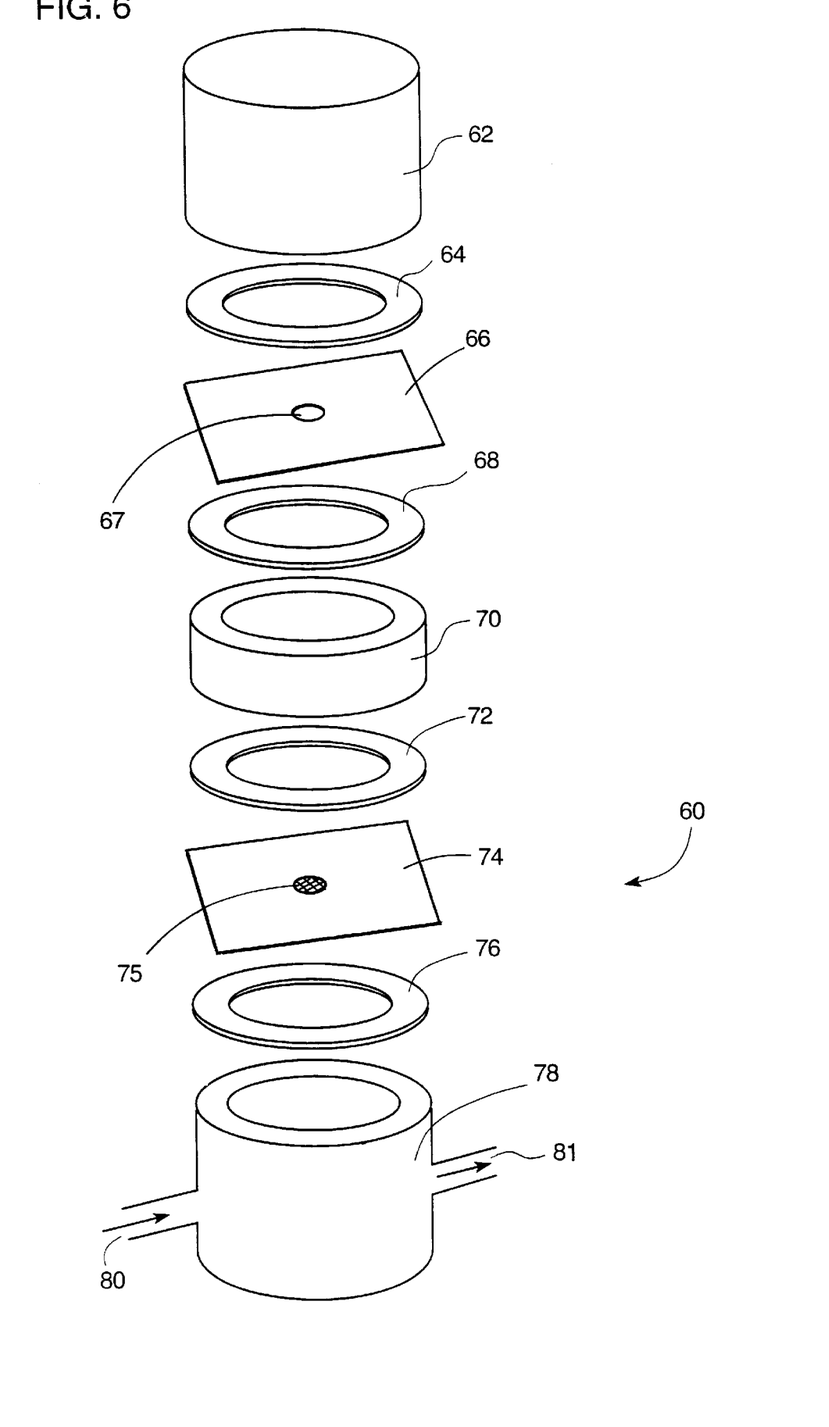
FIG. 6 is a perspective exploded view of an embodiment of a test apparatus.

FIG. 6 shows a test apparatus 60 that can be used to determine whether a candidate system will be useful for delivering a therapeutic agent as described herein. Device 60 includes an upper housing 62, an seal 64 (e.g., an o-ring seal), an electrically conductive sheet 66 (e.g., a platinum sheet) having a hole 67, a seal 68 (e.g., an o-ring seal), a spacer housing 70, a seal 72 (e.g., an o-ring seal), an electrically conductive sheet 74 (e.g., a platinum sheet), a seal 76 (e.g., an o-ring seal), and a lower housing 78 with a flow tube inlet 80 and a flow tube outlet 81. Sheet 74 contains a region 75 with pores that are filled with an electroactive polymer and BETA. The electroactive polymer is associated with the pores (e.g., having a diameter of from about three micrometers to about five micrometers), and the BETA is associated with the electroactive polymer.

A solution containing a material of interest (e.g., a therapeutic agent) is disposed in the upper, housing and a solution containing an analyte flows from flow tube inlet 80 to flow tube outlet 81. As the analyte-containing solution flows through tube 80, the analyte can interact with the BETA (e.g., via a redox reaction).

If a redox reaction between the BETA and analyte occurs, the size of the electroactive polymer decreases, increasing the ability of the solution contained in upper housing 62 to pass through the pores in sheet 74. At the same time, the electrical current formed by the reaction can be used to control a mechanism for increasing the pressure head on the solution contained in upper housing 62 (e.g., by controlling a pump, or by controlling the bias on a platinum/NAFION electrode plate on the upper portion of housing 62 which passes oxygen formed by water electrolysis caused by the electrical current), which also increases the ability of the solution to pass through the pores in sheet 74. This can increase the concentration of the material of interest (e.g., therapeutic agent) in the solution passing through flow tube outlet 81, which can be measured using techniques known to those skilled in the art (e.g., spectrophotometry).

If a redox reaction between the BETA and analyte does not occur, the ability of the solution contained in upper housing 62 to pass through the pores in sheet 74 should not increase, and an increase in the concentration of the material of interest passing through outlet 81 should not increase as a result of an interaction between the analyte and the BETA.

EXAMPLES

Example 1
Coating a Nucleopore7 Membrane with Platinum

A NUCLEOPORE7 membrane is pressed against the cooling plate of an Edwards S150B sputtercoater using a template with an opening that is slightly smaller than the diameter of the membrane. Platinum is then be applied to a thickness of 100–400 nm by sputtering under an argon pressure of 8 nBar and using a sputtering current of 50 mA. The thickness of the layer can be measured with an Edwards FTM5 unit.

Example 2
Oxidizing Chemical Polymerization of Pyrrole

Pyrrole is polymerized in the pores of a NUCLEOPORE7 membrane (25 mm in diameter) by allowing about 4 ml of an aqueous 2 M $FeCl_3$ solution and about 1 ml of an aqueous 0.6 M pyrrole solution to precipitate. This is carried out by positioning an injection syringe, which is filled with the iron chloride solution, vertically and mounting a standard membrane holder thereon. The membrane rests on the holder and can be weighted down with a rubber ring. The level of oxidizing iron (III) chloride solution in the syringe is raised until it just touches the membrane resting on the holder, and 1 ml of the pyrrole solution is applied to the membrane. The polymerization time is measured from the time this solution is applied. For NUCLEOPORE7 membranes having a diameter of 0.8 im and a pore density of $3\times10^7$ pores/$cm^2$, the polymerization can be continued for 1–10 minutes, after which time the membrane can be removed from the holder and rinsed with water or a phosphate buffer.

Example 3
Imobilization of Glucose Oxidase

Enzyme is immobilized on members prepared as described in Examples 1 and 2, and having an original pore diameter of 800 and 1000 nm. For enzyme immobilization, such a platinum- and pyrrole-coated member can be added to about 4 ml of a 5 mg/ml solution of glucose oxidase and incubated with shaking on a Gyratory Shaker Model G2 (New Brunswick Scientific). The immobilization reaction is continued for at least 30 minutes at 4EC. The membrane (serving as the member) can then be rinsed in PBS (pH=6.5) and dried overnight at 4EC. Drying takes place in a desiccator under normal pressure and in the presence of $CaCl_2$.

Example 4
Testing the Device

The activity of glucose oxidase, following application to the polymer-coated member as described above, is determined with a three-electrode cell containing 15 ml 0.1 M phosphate buffer (pH=6.5), 5 mM benzoquinone, and 0.5 M glucose. The glucose solution is allowed to mutarotate for at least 24 hours. The is carried our using a Pt rotary disc electrode (RDE) provided with an Electrocraft Corporation Model E550 motor and an E552 speed control unit.

A potential of 0.350 V ($Ag/Ag^+$ reference) is applied to the Pt working electrode, which is rotated at 3000 rpm. A spiral-shaped Pt electrode can be used as an auxiliary electrode, and the solution is flushed with argon before each test. During the test, the solution is blanketed with argon.

Electrochemical measurements are carried out using an Autolab potentiostat, which is controlled by a personal computer and General Purpose Electrochemical System (GPES) software (Eco Chemie, The Netherlands). The current output is recorded using a Yew 3056 pen recorder. The actual test is carried out by recording the current output of the RDE on submerging the sample membrane in the above-mentioned solution.

Various modifications and alterations to the above-described devices and methods are also contemplated by the invention. For example, in certain embodiments, a mediator can be used to assist in transferring electric charge between the membrane and the electroactive polymer and/or between the analyte and the electroactive polymer. Such mediators are well known to those skilled in the art and are disclosed, for example, in, for example, U.S. Pat. Nos. 5,126,034; 5,509,410; 5,628,890; 5,658,444; 5,682,884; 5,710,011; 5,727,548; and 5,849,174, and Szentrimay et al., ACS Symposium Series 438, chapter 9, p. 143, 1977 (D. T. Sawyer, ed.), which are hereby incorporated by reference.

In some embodiments, a device can include more than one member. In these embodiments, one or more of the members can include one or more pores, and one or more of the pores can include an electroactive polymer with or without a BETA associated thereto.

While the foregoing discussion has generally related to the use of one electroactive polymer in a device, more than one electroactive polymer can also be used. Similarly, while the foregoing discussion has generally related to the use of one BETA, more than one BETA can also be used. In certain embodiments, the device can contain more than one electroactive polymer and more than one BETA.

It is to be understood that while certain embodiments of the invention have been described herein, the invention is not limited by this description. Other embodiments are in the claims.

What is claimed is:

1. A device, comprising:
    a member having a pore passing therethrough;
    an electroactive polymer disposed so that when the electroactive polymer has a first state of charge a therapeutic agent has a first ability to pass through the pore, and when the electroactive pore has a second state of charge different from the first state of charge the therapeutic agent has a second ability to pass through the pore different than the first ability to pass through the pore; and
    a BETA associated with the electroactive polymer,
    wherein the electroactive polymer is at least partially disposed within the pore.

2. The device of claim 1, wherein the electroactive polymer is at least partially disposed outside the pore.

3. The device of claim 1, wherein the BETA is associated with the electroactive pore so that electronic charge can be transferred between the BETA and the electroactive pore.

4. The device of claim 1, wherein the BETA is associated with the electroactive polymer by an association selected from the group consisting of crosslinking, ionic bonding, covalent bonding and combinations thereof.

5. The device of claim 1, wherein the BETA comprises an enzyme.

6. The device of claim 1, wherein the BETA comprises glucose oxidase.

7. The device of claim 1, further comprising a mediator.

8. The device of claim 7, wherein the mediator mediates charge transfer between the electroactive pore and the member.

9. The device of claim 7, wherein the mediator mediates charge transfer between the electroactive pore and an analyte.

10. The device of claim 1, further comprising a reservoir in fluid communication with the pore.

11. The device of claim 10, further comprising a therapeutic agent disposed within the reservoir.

12. The device of claim 1, wherein the first state of charge has a smaller absolute value than the second state of charge.

13. The device of claim 12, wherein the first ability of the analyte to pass through the pore is greater than the second ability of the analyte to pass through the pore.

14. The device of claim 1, wherein the electroactive polymer comprises a polymer comprising a component selected from the group consisting of thiophen, derivatives of thiopen, phenylene, derivatives of phenylene, diamine, derivatives of diamine, pyrrole, derivatives of pyrrole, aniline, derivatives of aniline, and combinations thereof.

15. The device of claim 14, wherein the BETA comprises glucose oxidase.

16. The device of claim 1, wherein the membrane is a layer of a material.

17. A device, comprising:
   a member having a pore passing therethrough;
   an electroactive polymer disposed so that when the electroactive polymer has a first state of charge a therapeutic agent has a first ability to pass through the pore, and when the electroactive pore has a second state of charge different from the first state of charge the therapeutic agent has a second ability to pass through the pore different than the first ability to pass through the pore; and
   a BETA associated with the electroactive polymer,
   wherein the BETA comprises glucose oxidase.

18. The device of claim 17, wherein the electroactive polymer is at least partially disposed outside the pore.

19. The device of claim 17, wherein the BETA is associated with the electroactive pore so that electronic charge can be transferred between the BETA and the electroactive pore.

20. The device of claim 17, wherein the BETA is associated with the electroactive polymer by an association selected from a group consisting of crosslinlking, ionic bonding, covalent bonding and combinations thereof.

21. The device of claim 17, further comprising a mediator.

22. The device of claim 21, wherein the mediator mediates charge transfer between the electroactive pore and the member.

23. The device of claim 21, wherein the mediator mediates charge transfer between the electroactive pore and an analyte.

24. The device of claim 17, further comprising a reservoir in fluid communication with the pore.

25. The device of claim 24, further comprising a therapeutic agent disposed within the reservoir.

26. The device of claim 17, wherein the first state of charge has a smaller absolute value than the second state of charge.

27. The device of claim 26, wherein the first ability of the analyte to pass through the pore is greater than the second ability of the analyte to pass through the pore.

28. The device of claim 17, wherein the electroactive polymer comprises a polymer comprising a component selected from the group consisting of thiophen, derivatives of thiopen, phenylene, derivatives of phenylene, diamine, derivatives of diamine, pyrrole, derivatives of pyrrole, aniline, derivatives of aniline, and combinations thereof.

29. The device of claim 17, wherein the membrane is a layer of a material.

30. A device, comprising:
   a member having a pore passing therethrough;
   an electroactive polymer disposed so that when the electroactive polymer has a first state of charge a therapeutic agent has a first ability to pass through the pore, and when the electroactive pore has a second state of charge different from the first state of charge the therapeutic agent has a second ability to pass through the pore different than the first ability to pass through the pore;
   a BETA associated with the electroactive polymer; and
   a mediator that mediates charge transfer between the electroactive pore and the member.

31. The device of claim 30, wherein the electroactive polymer is at least partially disposed outside the pore.

32. The device of claim 30, wherein the BETA is associated with the electroactive pore so that electronic charge can be transferred between the BETA and the electroactive pore.

33. The device of claim 30, wherein the BETA is associated with the electroactive polymer by an association selected from a group consisting of crosslinking, ionic bonding, covalent bonding and combinations thereof.

34. The device of claim 30, wherein the BETA comprises an enzyme.

35. The device of claim 30, further comprising a reservoir in fluid communication with the pore.

36. The device of claim 35, further comprising a therapeutic agent disposed within the reservoir.

37. The device of claim 30, wherein the first state of charge has a smaller absolute value than the second state of charge.

38. The device of claim 37, wherein the first ability of the analyte to pass through the pore is greater than the second ability of the analyte to pass through the pore.

39. The device of claim 30, wherein the electroactive polymer comprises a polymer comprising a component selected from the group consisting of thiophen, derivatives of thiopen, phenylene, derivatives of phenylene, diamine, derivatives of diamine, pyrrole, derivatives of pyrrole, aniline, derivatives of aniline, and combinations thereof.

40. The device of claim 39, wherein the BETA comprises glucose oxidase.

41. The device of claim 30, wherein the membrane is a layer of a material.

42. A device, comprising:
   a member having a pore passing therethrough;
   an electroactive polymer disposed so that when the electroactive polymer has a first state of charge a therapeutic agent has a first ability to pass through the pore, and when the electroactive pore has a second state of charge different from the first state of charge the therapeutic agent has a second ability to pass through the pore different than the first ability to pass through the pore;
   a BETA associated with the electroactive polymer; and
   a mediator that mediates charge transfer between the electroactive pore and an analyte.

43. The device of claim 42, wherein the electroactive polymer is at least partially disposed outside the pore.

44. The device of claim 42, wherein the BETA is associated with the electroactive pore so that electronic charge can be transferred between the BETA and the electroactive pore.

45. The device of claim 42, wherein the BETA is associated with the electroactive polymer by an association selected from a group consisting of crosslinking, ionic bonding, covalent bonding and combinations thereof.

46. The device of claim 42, herein the BETA comprises an enzyme.

47. The device of claim 42, further comprising a reservoir in fluid communication with the pore.

48. The device of claim 47, further comprising a therapeutic agent disposed within the reservoir.

49. The device of claim 42, wherein the first state of charge has a smaller absolute value than the second state of charge.

50. The device of claim 49, wherein the first ability of the analyte to pass through the pore is greater than the second ability of the analyte to pass through the pore.

51. The device of claim 42, wherein the electroactive polymer comprises a polymer comprising a component selected from the group consisting of thiophen, derivatives of thiopen, phenylene, derivatives of phenylene, diamine, derivatives of diamine, pyrrole, derivatives of pyrrole, aniline, derivatives of aniline, and combinations thereof.

52. The device of claim 51, wherein the BETA comprises glucose oxidase.

53. The device of claim 42, wherein the membrane is a layer of a material.

54. A device, comprising:

a member having a pore passing therethrough;

an electroactive polymer disposed so that when the electroactive polymer has a first state of charge a therapeutic agent has a first ability to pass through the pore, and when the electroactive pore has a second state of charge different from the first state of charge the therapeutic agent has a second ability to pass through the pore different than the first ability to pass through the pore; and a BETA associated with the electroactive polymer, wherein the electroactive polymer comprises a polymer comprising a component selected from the group consisting of thiophen, derivatives of thiopen, phenylene, derivatives of phenylene, diamine, derivatives of diamine, pyrrole, derivatives of pyrrole, aniline, derivatives of aniline, and combinations thereof, and the BETA comprises glucose oxidase.

55. The device of claim 54, wherein the electroactive polymer is at least partially disposed outside the pore.

56. The device of claim 54, wherein the BETA is associated with the electroactive pore so that electronic charge can be transferred between the BETA and the electroactive pore.

57. The device of claim 54, wherein the BETA is associated with the electroactive polymer by an association selected from a group consisting of crosslinking, ionic bonding, covalent bonding and combinations thereof.

58. The device of claim 54, further comprising a reservoir in fluid communication with the pore.

59. The device of claim 58, further comprising a therapeutic agent disposed within the reservoir.

60. The device of claim 54, wherein the first state of charge has a smaller absolute value than the second state of charge.

61. The device of claim 60, wherein the first ability of the analyte to pass through the pore is greater than the second ability of the analyte to pass through the pore.

62. The device of claim 54, wherein the membrane is a layer of a material.

* * * * *